United States Patent [19]

Bombardelli et al.

[11] Patent Number: 6,150,140
[45] Date of Patent: Nov. 21, 2000

[54] PROCESS FOR THE BIOTRANSFORMATION OF COLCHICINOID COMPOUNDS INTO THE CORRESPONDING 3-GLYCOSYL DERIVATIVES

[75] Inventors: Ezio Bombardelli; Cesare Ponzone, both of Milan, Italy

[73] Assignee: Indena S.p.A., Milan, Italy

[21] Appl. No.: 09/230,116

[22] PCT Filed: Oct. 2, 1997

[86] PCT No.: PCT/EP97/05429

§ 371 Date: Jan. 28, 1999

§ 102(e) Date: Jan. 28, 1999

[87] PCT Pub. No.: WO98/15642

PCT Pub. Date: Apr. 16, 1998

[30] Foreign Application Priority Data

Oct. 7, 1996 [IT] Italy ................................. MI96A2063

[51] Int. Cl.⁷ ..................................................... C12P 19/44
[52] U.S. Cl. .............................. 435/74; 435/25; 435/119; 435/170
[58] Field of Search .......................... 435/74, 170, 252.5, 435/119

[56] References Cited

U.S. PATENT DOCUMENTS 3,090,729 5/1963 Bellet et al. .
3,812,011 5/1974 Okada et al. .

FOREIGN PATENT DOCUMENTS 1 344 157 10/1963 France .
2 154 396 5/1973 France .

OTHER PUBLICATIONS

Poulev et al., J. Ferment. Bioeng., vol. 79, 1, pp. 33–38, 1995.

Chemical Abstracts, vol. 119, No. 19, Nov. 8, 1993, Abstract No. 199644: Solet, Jean Michel et al., "Glucosylation of thiocolchicine by a cell suspension culture of *Centella asiatica*" (citing Phytochemistry (1993), 33(4), 817–20).

*Primary Examiner*—Irene Marx
*Attorney, Agent, or Firm*—Pennie & Edmonds LLP

[57] ABSTRACT

Colchicinoid compounds are transformed into the corresponding 3-O-glycosyl derivatives by means of *Bacillus megaterium* strains.

11 Claims, No Drawings

PROCESS FOR THE BIOTRANSFORMATION OF COLCHICINOID COMPOUNDS INTO THE CORRESPONDING 3-GLYCOSYL DERIVATIVES

FIELD OF THE INVENTION

The present invention relates to the biotransformation, effected by means of selected microbial strains, of colchicinoid compounds, into the respective 3-O-glycosyl derivatives. The process of the present invention provides colchicinoid compounds glycosylated exclusively at C-3 of the aromatic ring A, starting from colchicine, thiocolchicine or the derivatives thereof, in high yields and purity.

BACKGROUND OF THE INVENTION

The colchicinoid compounds glycosylated at C-3 of the benzene ring are of remarkable pharmacological importance for their high effectiveness or for the preparation of new medicaments.

In particular, thiocolchicoside (3-O-glucosylthiocolchicine) is an active ingredient of remarkably important use in the pharmaceutical field, mainly in the therapy of diseases of the muscle-skeletal system, and as starting materials for the preparation of novel antitumor, immunosuppressive, antipsoriasis and antiinflammatory medicaments.

A number of efforts for the preparation of 3-glycosylcolchicinoid compounds have been carried out in the past, either by means of chemical reactions or by biotransformation.

The chemical route consists in sequences of complex, non-specific reactions which lead to a mixture of glycosylated derivatives, some of which are inactive. Therefore, yields of the product specifically glycosylated at C-3 of the aromatic ring, are very low.

The biological approach substantially relates to the biotransformation of thiocolchicine, by culture of *Centella asiatica*, into monoglycosylated derivatives at C-2 and at C-3 of the aromatic ring; such a transformation is therefore not highly selective and provides scarce yields and productivity (Solet, J. M., et Al., Phytochemistry 33, 4, 817–820, 1993).

Other efforts to biotransform colchicinoid compounds gave simply demethylations of the methoxy groups bound to the aromatic ring (at C-2 and at C-3), and were always characterized by limited yields and productivity and by poor regioselectivity.

Thus, Hufford C. D. et al. (J. Pharm. Sc., 68, 10, 1239–1242, 1979), using *Streptomyces griseus* and/or *Streptomyces spectabilis*, and Bellet P. et al., (GB-923421, 1959), using different strains of Streptomyces and of other species of Bacteria and Fungi, tried to transform colchicine and its derivatives into the corresponding 3-demethylated derivatives. The results of these known methods confirm what is stated above in connection with the non-selectivity of the microbial enzymes involved at, for example the C-2, C-3 and C-10 positions of the alkaloid molecule. Moreover, the productivity levels of said catalytic systems are rather poor, due to the low conversion yields, the reduced substrate concentrations which can be used, and the frequent degradation of the tropolone ring.

More recently, Poulev et al. (J. Ferment. Bioeng. 79, 1, 33–38, 1995) have obtained the specific biotransformation using bacterial microorganisms, but still achieve poor yields and productivity.

Enzyme activity from microorganisms similar to the above mentioned ones (Streptomyces, Bacillus, etc.) have been applied to the biotransformation of other compounds, such as maytansinoids (U.S. Pat. No. 4,361,650: Izawa, M., et al., J. Antibiotics, 34, 12, 1587–1590, 1981). In this case the catalysed reaction also consists exclusively of a demethylation, characterized by low conversion yields and productivity.

The glycosyl transferase activity of α-amylase from *Bacillus megaterium* has been described (Brumm, P. J., et al., Starch, 43, 8, 319–323, 1991); the acceptor specificity of the transferase reaction (exclusively glucose or glucosides) being particularly high. Cyclodextrin-glucosyl transferases, produced by the same microbial source, catalyse an α-1,4-transglucosylation of rubusoside (13-O-β-D-glucosyl-steviol β-D-glucosyl ester), starting from starch. Also in this bioconversion the acceptor of the transferase reaction is the substrate glucide fraction (Darise, M., et al., Agric. Bioel. Chem., 48, 10, 2483–2488, 1984). Cyclodextringlycosyl transferases were previously used for the preparation of cyclodextrins G6, G7 and G8 from starch (Kitahata, S., Okada, S., Agric. Biol. (Chem., 38, 12, 2413–2417, 1974).

These examples evidence the high substrate specificity of the glycosyl transferase activity expressed by *Bacillus megaterium*, which involves only glucide acceptors and, therefore does not involve any reactions on secondary metabolites having a different, complex molecular structure, such as colchicinoids. In fact, no examples of the use of said microorganisms for the enzyme conversion of colchicinoids to 3-glycosyl derivatives are known.

SUMMARY OF THE INVENTION

Now it has been found that strains of *Bacillus megaterium* capable of growing in the presence of high concentrations colchicine and thiocolchicine, have an exceedingly high, very specific biotransformation activity of colchicinoid substrates into derivatives glycosylated exclusively at the C-3 position of the aromatic ring. Such a transformation takes place in very short times, and is characterized by surprisingly high yields.

Therefore, the invention relates to a process for the preparation of 3-O-glycosylcolchicinoid compounds of Formula (I)

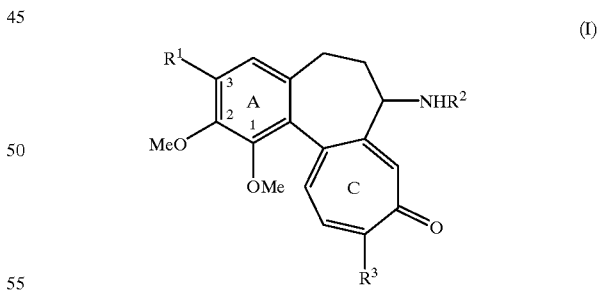

wherein $R^1$ is an O-glycosyde residue, $R^2$ is hydrogen or $C_1$–$C_7$ acyl, $R^3$ is $C_1$–$C_6$ alkoxy or $C_1$–$C_6$ thioalkyl, which comprises the biotransformation of compounds in which $R^1$ is OH or methoxy by means of *Bacillus megaterium*.

DETAILED DESCRIPTION OF THE PREFERRED EMBODIMENTS

*Bacillus megaterium* is a Gram-positive spore generating bacterium with a cell diameter greater than 1.0 μm; grows aerobically on a number of culture media; is catalase-positive; and hydrolysing gelatin.

Strains of *Bacillus megaterium* which can be used according to the invention proved capable of growing satisfactorily and of staying viable at high concentrations of colchicine and/or thiocolchicine (above 3 g/l), as evidenced by the examination of their growth and by microscope analysis.

Congeneric species, such as *Bacillus cereus*, at concentrations of substrate of 1.5 g/l evidence a difficulty in growing (absorbances of 15–25% of the control), which becomes even more marked at concentrations of 3 g/l, when dramatic autolysis occurs. Selected cultures of *Bacillus megaterium*, on the contrary, at the above mentioned concentrations can reach much higher growth levels (double to triple) compared with *Bacillus cereus*.

The high selectivity and efficiency of the biotransformation is surprising and unusual, as the yield levels range from 80% to 100%, usually about 90 to 95%.

Moreover, the microorganisms used in the bioconversion are capable of maintaining permanently the catalytic activity, even in repeated fermentation steps, therefore providing the specific bioconversion in fed-batch and continuous processes. Therefore this method provides high productivity and reproducibility levels.

The marked reaction regioselectivity assures, in addition to the remarkable production yields, a high quality and purity of the resulting product, thus providing it in a 100% purity, with simple downstream processing.

Further, important advantages of this invention are the reduced need for the steps of purification and recovery of the product, the economy of the process and the affordability and safety of use.

The operative sequences for the selection of the bacterial strains useful in the process of the invention comprise:

A) Selection of cultures of *Bacillus megaterium* capable of growing in the presence of high concentrations of colchicinic substrate, starting from natural sources or from collection strains.

B) Selection of the isolate from A), to verify the transformation activity of colchicines into the corresponding 3-O-glycosyl derivatives, by means of bioconversion assays on the specific substrates, administered in gradually increasing concentrations.

C) Microbiological characterization of the strains selected in B).

D) Gradual increase in the biotransformation yield, by means of a target-specific selection of the bacterial population from B).

E) Study and optimization of the critical fermentation parameters, to optimize the biotransformation.

F) Study and optimization of the methods for the conservation of the high-productivity cultures, to guarantee stable, homogeneous inocula for productive applications on the industrial scale.

G) Scale-up of the process in fermenter, in batch, fed-batch and continuous processes.

H) Working up and optimization of the methods for the downstream processing and for the recovery of the product.

Specifically, the microorganisms usable in the present invention can be selected starting from collection cultures obtained from strain deposit centers, or from soil samples of various origin, by selective recovery on different agar media containing an organic nitrogen source (peptones, yeast extracts, meat extracts, asparagine, etc), a carbon source (glycerin, starch, maltose, glucose, etc.), with pH of 5 to 8, preferably 6 to 7. The incubation temperature ranges from 20° to 45° C., preferably 28° to 40° C.

The capacity of the culture of growing in the presence of toxic concentrations of the colchicinic substrate to be transformed is evaluated by techniques of scalar dilution and plating in parallel, on different agarized substrates, a part of which was previously treated with colchicine or thiocolchicine, in concentrations from 0.1 to 3 g/l (so as to inhibit the growth of the main part of the microorganisms).

The colonies capable of growing in the described conditions are withdrawn using sterile means and placed on different agarized media, to verify their purity and the homogeneity of growth.

The culture media used for the conservation of the culture are typical microbiological substrates, containing organic nitrogen sources (peptones, yeast extracts, tryptone, meat extracts, etc.), a carbon source (glucose, maltose, glycerin, etc.), at a pH of 5 to 8, preferably 6 to 7. The incubation temperature ranges from 20° to 45° C., preferably 28° to 40° C.

The selected microorganisms are then assayed for the capability of growing in a submerged culture, in the presence of colchicinoid compounds, and of transforming the latter into the corresponding 3-glycosyl derivatives.

Said assays were carried out in 100 ml flasks containing 20 ml of liquid medium, with different medium formulations, comprising one or more organic nitrogen sources (yeast extracts, peptones, tryptone, casein hydrolysates, meat extract, corn-step liquor, etc.), one or more carbon sources (glucose, glycerol, starch, saccharose, etc.), inorganic phosphorous and nitrogen sources, and inorganic salts of various ions ($K^+$, $Na^+$, $Mg^{++}$, $Ca^{++}$, $Fe^{++}$, $Mn^{++}$, etc.).

The culture samples can optionally be subjected to mutagenic treatments, by means of the conventional mutagenesis techniques (irradiation with UV rays, etc.) to induce mutants having a specific bioconversion activity which can be evaluated with the same procedure as above.

Culture samples from each bioconversion assay, were analyzed to evaluate the production of 3-glycosyl derivatives, by means of TLC and HPLC chromatographies.

The capability to the selected microorganism of transform colchicinoid substrates into their respective 3-glycosyl derivatives was confirmed by means of bioconversion assays on flasks, in a 300 ml scale, in the same culture broths as used in the selection step.

The microorganisms which gave a positive response were used in tests for the optimization of the bioconversion, on different culture broths, in a 300 ml scale. The main cultural and fermentation parameters studied were: organic nitrogen sources, carbon sources, mineral salts, temperature, stirring-aeration, pH, incubation time, inoculum ratio, subculture steps, time of addition of the substrate to be transformed. The selected bacterial microorganisms, capable of affecting the biotransformation of the present invention, can grow on both solid and liquid culture substrates, containing one or more organic nitrogen sources, preferably yeast extract, meat extract, peptone, tryptone, casein hydrolysates, corn-steep liquor, etc.. Carbon sources useful for the growth and the biotransformation are glucose, fructose, saccharose, glycerol, malt extract, etc., preferably glucose, fructose and glycerin. The culture medium also contains inorganic phosphorous sources and salts of $K^+$, $Na^+$, $Mg^{++}$, $NH_4+$, etc..

The selected microorganisms can grow at temperatures from 20° to 45° C., preferably from 28° to 40° C., at pH between 5 and 8, preferably 6 to 7. In the same conditions, the considered microorganisms are capable of transforming the colchicinoid compounds into their corresponding 3-glycosyl derivatives. Said transformations occur in submerged culture, in flasks incubated on a rotating shaker, with stirring from 150 to 250 rpm.

Due to the particular kinetics of the biotransformation concerned, which is related to the microbial growth, the optimum conditions for the purposes of biotransformation are the same conditions which are optimum for the growth. Therefore, culture media useful to promote a good microbial growth, such as those based on the organic and inorganic components cited above, are also useful to achieve a good activity of biotransformation of the concerned substrate. The latter is added to the culture in the starting fermentation step.

The biotransformation of the invention is based on an enzyme conversion, which starts during the exponential phase of microbial growth and continues with a progression parallel to that of the growth; the maximum levels of conversion to 3-glycosyl derivative (very high: up to 95–100%) are reached within the first 24–30 hours. The regioselectivity of the biotransformation is absolute: no presence of 2-glycosyl derivatives has ever been evidenced. The resulting products are exclusively extracellular.

The biotransformation of the invention can be scaled up to fermenter level, keeping the culture conditions unchanged, in particular as far as culture medium, temperature and processing times are concerned. In order to obtain good growth, adequate levels of stirring-aeration are important, in particular aeration levels of 1–2 liters of air per liter of culture per minute (vvm), preferably of 1.5–2 vvm, are required.

The products resulting from the bioconversion are extracted from the culture broths after separation of the biomass from the liquid fraction by centrifugation and recovery of the supernatant, or by microfiltration and recovery of the permeate. The culture can be treated with alcohols, to achieve an optimum recovery of the product.

The purification and the recovery of the biotransformation products can be carried out using chromatographic techniques for the separation on absorption resins and elution with alcohols, preferably with methanol. The hydromethanol solutions containing the product can further be purified by extraction with lipofilic organic solvents, preferably with methylene chloride. After further treatments with mixtures of alcohols and organic solvents, the product can be obtained in the pure state from the resulting alcohol solutions by crystallization.

The biotransformation process is specific for substrates containing a tropolone group and can be applied to a number of colchicinoid compounds, such as colchicine, thiocolchicine, 3-demethylcolchicine, 3-demethylthiocolchicine, N-desacetylthiocolchicine and other variously substituted colchicines.

Other natural compounds lacking the tropolone are not glycosylated by *Bacillus megaterium*.

Glucose can be replaced by other sugars, such as fructose or galactose, without causing the loss of the glycosyl transferase activity.

The following examples disclose the invention in further detail.

EXAMPLES

Example 1

Aliquots of cultures of *Bacillus megaterium*, isolated from agriculture soil, are resuspended in 20 ml of sterile saline, and subjected to a scalar dilution to a 1:10.000,000 dilution factor. The suspensions at various dilutions are plated on LB-Agar culture medium and on LB-Agar added respectively with colchicine or thiocolchicine, to a final concentration of 2 g/l (see Table). The cultures are incubated at +28° C., for 3 days, in the dark. The colonies grown on the selective medium, and added with the colchicinoid, are isolated and purified by means of plating on non-selective medium; said samples are incubated as above, but for a shorter time (24 hours). Subsequently the cultures are transferred to the same agar medium, in a test-tube, and incubated as above for 24 hours.

Aliquots of cultures, selected as described, are used to inoculate 100 ml Erlenmeyer flasks containing 20 ml of culture medium ST (Table), to which colchicine or thiocolchicine was added, to a 0.4 mg/ml final concentration. Said cultures are incubated overnight at 28° C., on a rotary shaker, at 200 rpm.

The transformation of the colchicine substrate is checked by analysis of aliquots of culture broths, taken every 3 to 4 hours, by TLC on silica gel, with an acetone:ethyl acetate::water 5:4:1 eluent system.

After a 4 day incubation, aliquots of the cultures, which proved an evident catalytic activity towards the 3-glycosyl derivative, are recovered on plates, by means of scalar dilution as described above, for the preparation of novel inocula in test-tube. The biotransformation assay in the flask is repeated in the same conditions as above, but using markedly higher final concentrations of colchicine and thiocolchicine (1 mg/ml). The most active single cultures (substrate conversion equal to or higher than 80%) are used for the preparation of inocula in frozen cryotubes, as described in Example 3.

TABLE

Formulation of the culture media

| | |
|---|---|
| 1) LB-Agar (Sterilization: 121° C. × 20') - pH 7 | |
| Triptone | 10 g/l |
| Yeast extract | 5 g/l |
| NaCl | 10 g/l |
| Agar Agar | 15 g/l |
| 2) Broth ST (Sterilization: 121° C. × 20') - pH 7 | |
| Glucose | 20 g/l |
| Glycerol | 10 g/l |
| Peptone | 15 g/l |
| Yeast extract | 5 g/l |
| NaCl | 3 g/l |
| $NH_4Cl$ | 3 g/l |
| $K_2HPO_4$ | 8 g/l |
| $KH_2PO_4$ | 3 g/l |
| $MgSO_4.7H_2O$ | 0.5 g/l |

Example 2

The procedure described in Example 1 is repeated, starting from *Bacillus megaterium* cultures, deriving from the following collection strains (Deutsche Sammlung von Mikroorganismen, Braunschweig, Germany): DSM 90, 509, 322, 333, 1667, 1670, 1671.

The culture selected as in Example 1 and added with thiocolchicine (1 mg/ml) are incubated for 4 days in liquid culture: the TLC analysis detects the occurred transformation of the substrate into thiocolchicoside, with conversion yields varying from 50% (strain DSM 1671) to 70% (strain DSM 90), to 80% and above (strains DSM 333, DSM 509, DSM 1667, DSM 1670).

Example 3

Aliquots of culture samples in test-tube, selected as described in the above example, are used to inoculate 100 ml Erlenmeyer flasks containing 20 ml of broth ST.

The broth cultures are incubated at +30° C., on a rotary shaker at 200 rpm, overnight. After incubation, the cultures are added with a glycerol sterile solution to a 20% final concentration. The cultures are then dispensed into 2 ml cryotubes and immediately immersed in liquid nitrogen.

After some days, 10% of the cultures are thawed quickly at 37° C. Aliquots of each cryotube are used to inoculate 100 ml Erlenmeyer flasks containing 20 ml of medium ST, which are subsequently incubated at +28° C., overnight (preculture), at 200 rpm. After incubation, 2 ml of each preculture are transferred in using sterile means into 20 ml of fresh medium ST, to which colchicine or thiocolchicine was added to a 1 g/l final concentration. The biotransformation is carried out and checked using the conditions described in Example 1. The analysis confirmed that the transformation of the substrate into the 3-glycosyl derivative occurred in the quantitative terms described above (80% and higher), thus proving the catalytic stability of the frozen cultures.

Parallel controls of the broth cultures, plated on LB Agar immediately after thawing, confirm the viability, homogeneity and purity of the frozen cultures.

Example 4

Aliquots of cultures in cryotube, after thawing, are used to inoculate 300 ml Erlenmeyer flasks containing 50 ml of medium ST (preculture). After incubation overnight at 30° C., 250 rpm, 5 ml of preculture are transferred into 50 ml of the same medium to which colchicine has been added a 1 g/l final concentration. The cultures are incubated for 2 days, in the same conditions as described above. Every 4 hours, samples are taken to evaluate the growth level (measuring the absorbance at 600 nm), the colchicoside production (TLC and HPLC), the sterility (on LB Agar), and for the microscope morphological examination.

For the HPLC analysis, 1 ml fractions of culture broths are added with 9 ml of methanol and centrifuged at 13,000 rpm for 2 minutes. The colchicoside content of the supernatant is analyzed by reverse phase HPLC, with isocratic elution, by means of the water:acetonitrile 80:20 system eluent.

The HPLC analysis proves that the conversion of the colchicine into colchicoside follows a progression parallel to that of the growth. After about 26 hours of incubation, the bioconversion is completed.

The colchicoside final yield ranges from 80% to 85%.

Example 5

The procedure described in Example 4 is repeated, wherein thiocolchicine instead of colchicine is added to the cultures, at the same final concentration (1 g/l).

The growth and production responses of the cultures are similar to those obtained with colchicine, with thiocolchicoside yields of about 90%.

Example 6

The procedure described in Example 4 is repeated, wherein 3-demethylthiocolchicine instead of colchicine is added to the culture, at the same final concentration (1 g/l). The growth and production responses of the cultures are similar to those obtained above, with thiocolchicoside yields of about 90%.

Example 7

The procedure described in Example 4 is repeated, wherein N-formylthiocolchicine instead of colchicine is added to the culture, at the same final concentration (1 g/l). The growth and production responses of the cultures are similar to those obtained above, with thiocolchicoside yields of about 90%.

Example 8

One liter of ST broth in Erlenmeyer flask is inoculated with a cryotube culture of the strain DSM 1670. The flasks are incubated overnight at +30° C., 250 rpm. The inoculum is transferred using sterile means into a 14 l fermenter, containing 9 l of sterile broth ST, to which thiocolchicine has been added to a 1 g/l final concentration. The fermentation is carried out keeping suitable levels of stirring-aeration (stirring up to 900 rpm; aeration 1 to 1.5 vvm, depending on the culture growth). Every 2 hours, samples from the culture broths are taken and subjected to the following analysis:

Optical density (OD) at 600 nm,

Sterility and purity analysis of the strain on LB Agar;

Microscope morphology (Gram stain);

Analysis of the thiocolchicoside content, by TLC and HPLC.

After 28 hours of fermentation, the transformation into thiocolchicoside is almost finished. The final yield is about 90%.

Example 9

The procedure described in Example 8 is repeated, but after 28 hours of fermentation, only 90% of the culture broths are recovered, to extract the product (fraction 1). The residual 10% is added using sterile means to the fermenter with 9 l of fresh sterile medium ST containing 10 g of thiocolchicine. The fermentation is carried out as described in Example 8. After 26 hours, 9 l of culture broths are collected and extracted (fraction 2). The residual volume of culture broths is added using sterile means to 9 more liters of sterile fresh medium ST containing fresh thiocolchicine (10 g). The fermentation is carried out as above. After 26 hours the culture broth is collected completely and extracted (fraction 3). The biotransformation activity of the strain remained stable for all of the three runs, with conversion yields of about 90%, and with a substantially triple total production of thiocoichicoside, compared with that obtained in the single batch process.

Example 10

The final culture broth from the fermentation (total volume: about 27 l) is subjected to cross-flow microfiltration, on a 0.22 µm ceramic cartridge, to separate the cells from the broth. The permeate is absorbed on a column filled with a HP 21, Mitsubishi absorption resin. After washing with water, the product is eluted with methanol. The methanol eluate is concentrated to dryness under vacuum, then redissolved in methanol. After repeated extractions with methylene chloride, the alcohol fraction is concentrated to dryness and redissolved in an ethanol-methylene chloride, 1:1 mixture. After clarification with silica gel, the solution is concentrated under vacuum; methylene chloride is then substituted with ethanol. The resulting suspension is concentrated and left to crystallize. A second crystallization with ethanol is carried out after further redissolving of the solid in ethanol-chloroform mixtures and clarifying the mixture on silica gel.

The resulting product, analyzed by HPLC, C-NMR, H-NMR and mass spectral analysis, turns out to be the same as the thiocolchicoside standard.

What is claimed is:

1. A process for preparing a compound of Formula (I)

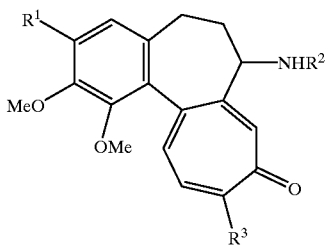

Formula (I)

wherein $R^1$ is an O-glycoside residue, $R^2$ is hydrogen or $C_1$–$C_7$ acyl, and $R^3$ is $C_1$–$C_6$ alkoxy or $C_1$–$C_6$ thioalkyl, comprising:

contacting a compound of Formula (II)

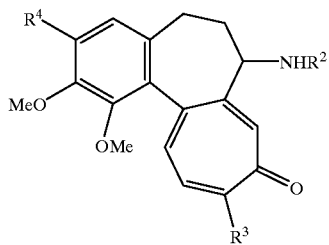

Formula (II)

wherein $R^4$ is hydroxy or methoxy, $R^2$ is hydrogen or $C_1$–$C_7$ acyl, and $R^3$ is $C_1$–$C_6$ alkoxy or $C_1$–$C_6$ thioalkyl with a strain of *Bacillus megaterium* at a temperature of between about 20° C. and about 45° C., at a pH level of between about 5 and about 8, and for a time sufficient to produce a compound of Formula (I); and isolating the compound of Formula (I).

2. The process of claim 1 further comprising selecting the strain of *Bacillus megaterium* to be DSM 90, DSM 509, DSM 322, DSM 333, DSM 1667, DSM 1670, or DSM 1671, as deposited with Deutsche Sammlung von Mikroorganismen, Braunschweig, Germany.

3. The process of claim 1 further comprising contacting the compound of Formula (II) with a strain of *Bacillus megaterium* in a culture comprising one or more organic nitrogen sources, one or more carbon sources, and one or more inorganic phosphorous and nitrogen sources.

4. The process of claim 3 wherein the culture is a submerged culture.

5. The process of claim 3 further comprising adjusting the concentration of the compound of Formula (I) in the culture to be between 0.1 and 3 grams/liter.

6. The process of claim 4 further comprising maintaining the culture at a temperature of between 28° C. and 40° C. and at a pH of between 6 and 7.

7. The process of claim 6 wherein the one or more carbon sources are selected from the group consisting of glucose, fructose, saccharose, glycerol, and malt extract.

8. The process of claim 6, wherein the one or more organic nitrogen sources are selected from the group consisting of yeast extracts, meat extracts, peptone, tryptone, casein hydrolysates, and corn-steep liquor.

9. The process of claim 6, further comprising one or more inorganic salts of ions selected from the group consisting of $K^+$, $Na^+$, $Mg^+$, $Ca^+$, $Fe^+$, and $Mn^+$.

10. The process of claim 1 further comprising selecting the compound of Formula (II) such that $R^4$ is methoxy, $R^2$ is methyl ketone, and $R^3$ is methoxy.

11. The process of claim 1 further comprising selecting the compound of Formula (II) such that $R^4$ is methoxy, $R^2$ is methyl ketone, and $R^3$ is thiomethyl.

* * * * *